US 6,585,146 B2

(12) United States Patent
Shepard

(10) Patent No.: US 6,585,146 B2
(45) Date of Patent: Jul. 1, 2003

(54) AUTOMATED NON-DESTRUCTIVE WELD EVALUATION METHOD AND APPARATUS

(75) Inventor: Steven M. Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 0 days.

(21) Appl. No.: 09/754,919

(22) Filed: Jan. 5, 2001

(65) Prior Publication Data

US 2002/0134817 A1 Sep. 26, 2002

Related U.S. Application Data

(60) Provisional application No. 60/174,794, filed on Jan. 6, 2000.

(51) Int. Cl.[7] .............................................. B23K 31/12
(52) U.S. Cl. ............................. 228/104; 228/9; 228/105
(58) Field of Search ................................. 228/102, 103, 228/104, 8, 9, 105; 356/51

(56) References Cited

U.S. PATENT DOCUMENTS

| 4,214,164 | A | * | 7/1980 | Traub et al. |
| 4,647,220 | A | * | 3/1987 | Adams et al. |
| 4,663,513 | A | * | 5/1987 | Webber |
| 4,792,683 | A | * | 12/1988 | Chang et al. |
| 4,854,724 | A | | 8/1989 | Adams et al. |
| 5,292,195 | A | * | 3/1994 | Crisman, Jr. |
| 5,552,575 | A | * | 9/1996 | Doumanidis |
| 5,651,903 | A | * | 7/1997 | Shirk |
| 5,721,415 | A | * | 2/1998 | Fortmann et al. |
| 5,963,662 | A | * | 10/1999 | Vachtsevanos et al. |
| 5,968,376 | A | * | 10/1999 | Shirk |
| 6,137,860 | A | * | 10/2000 | Ellegood et al. |
| 6,153,848 | A | | 11/2000 | Nagae et al. |

FOREIGN PATENT DOCUMENTS

| JP | 403060882 A | * | 3/1991 |
| JP | 02000167686 A | * | 6/2000 |

OTHER PUBLICATIONS

WO 01/50116 A1 Shepard (Jul. 12, 2001).*

* cited by examiner

Primary Examiner—Tom Dunn
Assistant Examiner—Kiley Stoner
(74) Attorney, Agent, or Firm—Rader, Fishman & Grauer PLLC

(57) ABSTRACT

A method and apparatus for automated, non-destructive evaluation of spot welds includes a device for heating a sample containing a spot weld, an infrared camera for detecting changes in the surface temperature of the weld, and a computer to acquire and analyze data from the camera. In one embodiment, the sample is heated on one side and the time-temperature characteristic is monitored as the heat travels through the sample and the spot weld. The computer generates a histogram that represents the relationship between a particular time-temperature characteristic and the number of pixels exhibiting that characteristic, thereby representing the quality and size of the weld nugget. By generating a histogram corresponding to weld quality, the inventive apparatus and method provides an objective weld quality indicator and allows automation of the evaluation process.

38 Claims, 7 Drawing Sheets

AUTOMATED NON-DESTRUCTIVE WELD EVALUATION METHOD AND APPARATUS

This application claims the benefit of U.S. Provisional Application No. 60/174,794 filed Jan. 6, 2000.

TECHNICAL FIELD

The invention is directed to weld evaluation, and more particularly to a method and apparatus for non-destructive evaluation of weld integrity.

BACKGROUND ART

Testing weld integrity is an important part of many manufacturing processes, such as in automotive manufacturing where spot welds are formed in steel or aluminum sheet metal. Current systems evaluate weld integrity by prying the weld apart, visually inspecting the weld, and measuring the diameter of the weld nugget (e.g., the region where the welding process has formed a true metallurgical bond).

The problem with known evaluation systems, however, is that the weld is destroyed during the evaluation process because the weld must be opened to be visually inspected and measured. Visual inspection also introduces an element of subjective evaluation, creating the potential for inconsistent evaluation results between samples. Further, currently known evaluation methods cannot be automated because they require a great deal of human intervention and/or user input.

There is a need for a system that can conduct non-destructive evaluation of weld integrity and that offers an automation option. There is also a need for a system and method that can evaluate welds using objective criteria to ensure consistent evaluation results between samples.

SUMMARY OF THE INVENTION

Accordingly, the present invention is directed to an apparatus and method for non-destructive evaluation of welds. The apparatus generally includes a heater that heats the weld, a camera that detects changes in the surface temperature of the weld, and a computer that acquires and analyzes time-temperature data from the camera as the weld temperature varies over time.

The inventive method includes heating one surface of the sample and starting data collection, in the form of image data, using the camera at the same time the flash begins. The method then includes examining the time-temperature history of individual sections in the image obtained from the camera, such as each pixel in the image. In one embodiment, the method measures heat flux (i.e. heat per unit time per unit area) during the time interval between the initiation of the flash and the time a selected surface of the sample reaches a predefined temperature. At least one time-temperature characteristic in the time-temperature history is then compared with objective criteria to evaluate the weld quality.

DETAILED DESCRIPTION OF THE PREFERRED EMBODIMENTS

Figure 1:
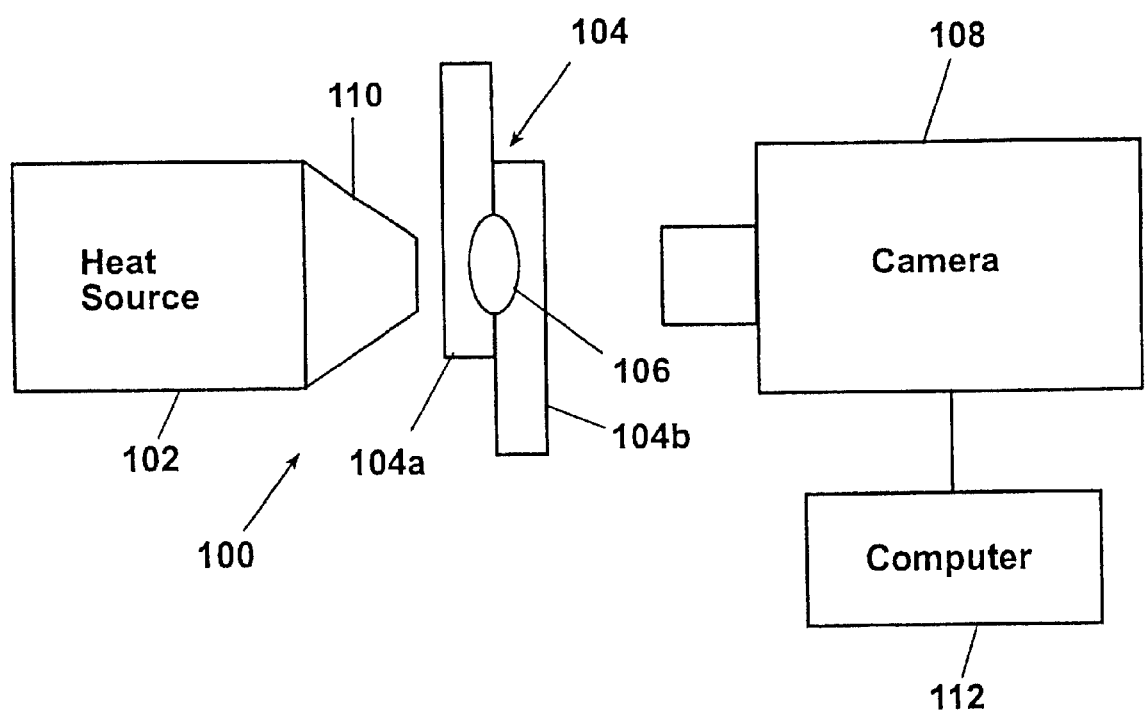
FIG. 1 is a schematic drawing of a first embodiment of a weld evaluation apparatus according to the present invention.
Figure 2:
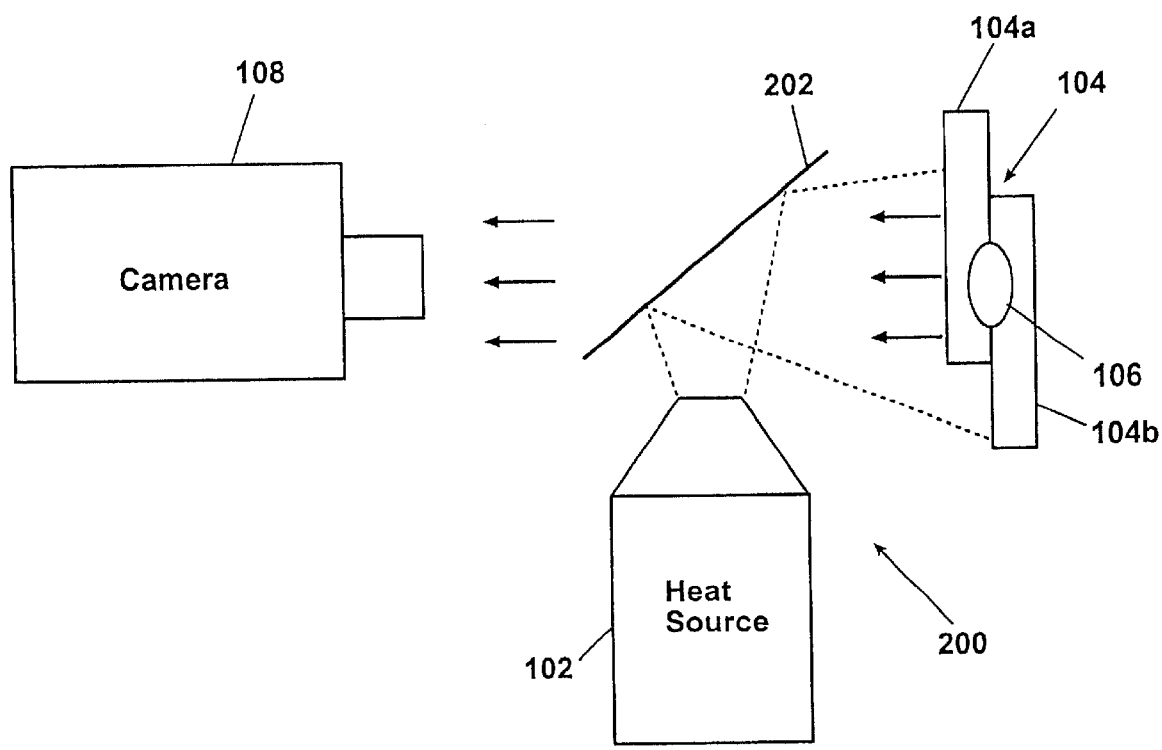
FIG. 2 is a schematic drawing of a second embodiment of a weld evaluation apparatus according to the present invention.

FIGS. 1 and 2 illustrate two possible configurations of a non-destructive weld evaluation apparatus according to the present invention. FIG. 1 illustrates an apparatus 100 having a heat source, such as a flashlamp 102, disposed adjacent side 104a of a sample 104 having a weld nugget 106 to be evaluated. Preferably, the same should be capable of generating an energy density of 2 kilojoules/cm$^2$ or greater in a duration of less than 5 milliseconds. Although the description herein assumes that the heat source is a flash lamp, any device capable of localized heating of the sample can be used, such as a pulsed laser optically coupled to an optical fiber, or a light source coupled with a focusing lens. A heat-sensitive camera, such as an infrared (IR) camera 108, is disposed opposite the other side 104b of the sample 104 in the embodiment of FIG. 1. The flashlamp 102 is preferably focused to a spot size that is roughly equal to the weld nugget's 106 diameter. Further, a conical snout 110 may be mounted on the flashlamp 102 to concentrate the flashlamp beam onto the sample 104.

The IR camera 108 is preferably a high-speed focal plane array camera operating in the 2–5 micron spectral range, although other spectral ranges can be used. Data is sent from the IR camera 108 to a computer 112 for capturing the camera data, analyzing the data and either displaying the results on a display (not shown) or sending the data electronically to other devices (not shown). The specific manner in which data is sent to the computer 112 is not significant to the inventive concept. Although, in a typical system, 12-bit digital data can be obtained directly from the IR camera 108 using a digital interface PC card, the same result can be accomplished using analog data. The camera acquisition rate is preferably high enough to measure the rate of heat flow through the sample (e.g. 200 Hz or higher).

To inspect the sample 104 using the configuration shown in FIG. 1, the flashlamp 102 flash-heats the sample 104 on surface 104a. Data collection by the IR camera 108 on the opposite surface 104b of the sample using the IR camera 108 begins at the same time the flash occurs and continues as the heat travels from one side of the sample 104, through the weld nugget, toward the other side of the sample 104. Preferably, data is collected until after surface 104b reaches maximum temperature (typically this takes a few hundred milliseconds).

Once the camera 108 and computer 112 collect the data, a software routine is employed to examine a time-temperature characteristic from the time-temperature history of each pixel in the image. More particularly, a dedicated software program operating on computer 112, monitors a time interval between the initiation of the flash and the time at which the non-heated surface 104b reaches a maximum temperature.

FIG. 2 illustrates a second possible configuration for the inventive apparatus. The apparatus 200 shown in FIG. 2 includes a mirror 202 that reflects infrared light and transmits visible light. As can be seen in FIG. 2, both the camera 108 and the flashlamp 102 are disposed on the same side 104a of the sample 104 rather than on opposite sides, as in FIG. 1. In this case, the visible light generated by the flashlamp 102 is reflected by the mirror 202 onto the sample's surface 104a to heat the sample 104, and the heat radiating from the sample 104, in turn, travels through the mirror 202 to the IR camera to be captured as an image.

Because the camera 108 and the flashlamp 102 are disposed on the same side 104a of the sample 104 in the embodiment shown in FIG. 2, the time-temperature history will be different from that of the previous embodiment; in this embodiment, the time-temperature history will reflect an instantaneous temperature rise from the flashlamp heat and then a gradual cooling. However, the time-temperature histories obtained from both embodiments can be analyzed in the same manner.

Figure 3:
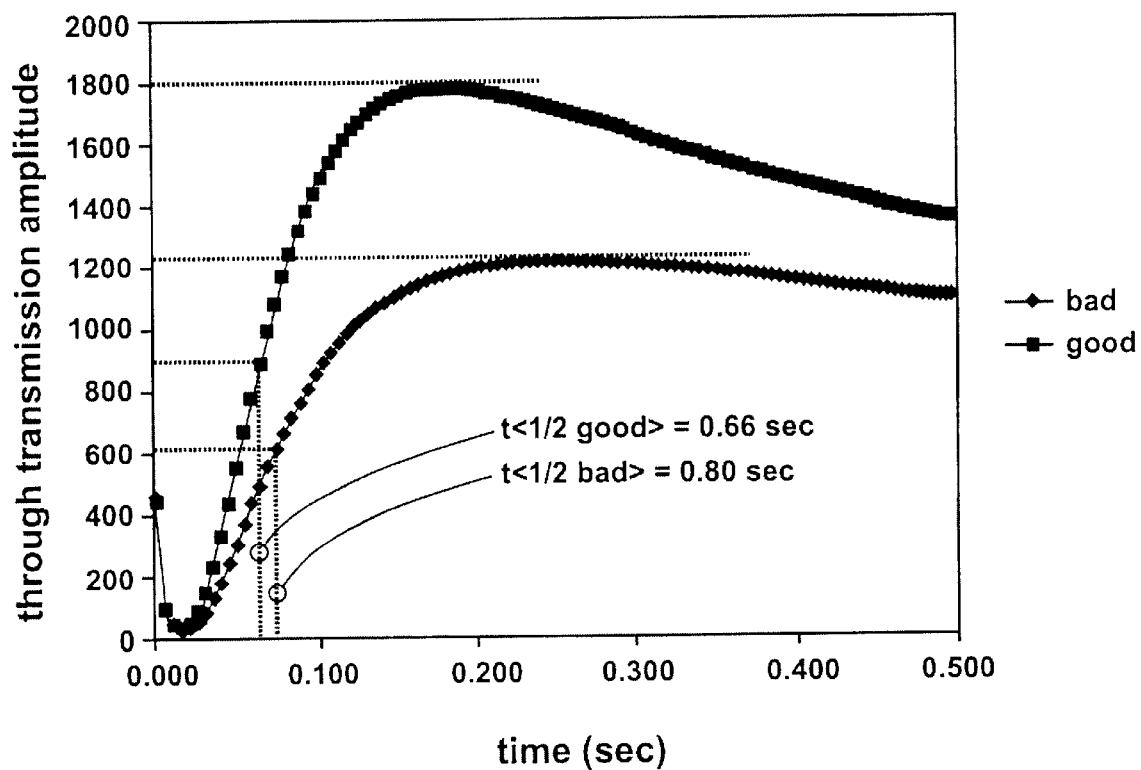
FIG. 3 is an example of a time-temperature history of a center of a spot weld.

Referring to FIG. 3, the time-temperature history is used for weld evaluation in the present invention because the time-temperature characteristics in the history accurately reflect weld quality. As is known in the art, in an actual weld joint between two combined and properly welded pieces of metal the constituent pieces melt and then resolidify to form a single, continuous weld nugget, rather than two pieces that are merely in mechanical contact, but with a discontinuous thermal interface. As a result, the flux of heat (amount of heat per unit time per unit area) through two properly welded pieces will be greater than the flux through the constituent pieces joined by some mechanical means (e.g. pressure, clamping, adhesive, etc.). Furthermore, a weld that is less than perfect may not have sufficient depth, or may contain cracks, inclusions or coating residue, porosity due to trapped gas or other anomalies that will serve to decrease the heat flux through the weld.

The expected maximum allowable half-max time (time that the side opposite the heat source reaches ½ of its maximum temperature) for a weld may be determined empirically or may also be estimated from a known formula for flash thermal diffusivity measurement, so that $$t_{1/2\,max} = \frac{1.38\,L^2}{\pi^2 \alpha}$$

where $\alpha$ and L are the thermal diffusivity and the thickness of the sheet metal, respectively. Generating the time-temperature history and its associated characteristics condenses the entire IR image frame sequence for a given weld IR into a single, easy-to-analyze data structure (either an image or the equivalent histogram) that indicates the quality and size of the weld nugget. Although the weld quality can be determined from the maximum amplitude, ascending slope, descending slope, or maximum time in the time-temperature history, a preferred time-temperature characteristic for evaluating welds is a "half-max" time, which is the time at which the temperature for a given image section (e.g. a pixel) rises to half its maximum value. The half-max time is preferred because it can be measured precisely without extensive signal processing, is independent of signal amplitude, and is not adversely affected by noise. The specific manner in which a time-temperature history and characteristic is analyzed will be explained in greater detail below.

FIG. 3 illustrates one example of a time-temperature history for a point in the center of the nugget of two spot welds, one good and one bad, for explanatory purposes. The welds used in this example were formed from identical thicknesses of sheet steel and destructively evaluated via conventional visual inspection. As can be seen in the Figure, the maximum amplitude, ascending and descending slopes, and maximum time values differ for the two welds due primarily to the heat flow interruptions and resulting increased thermal transit time in the weld. Although any of these characteristics could be used to form an image, the half-max time is the preferred for weld evaluation, as noted above.

After measuring the time-temperature characteristic, such as the half-max time, for each pixel in the image, the computer may generate a map of the pixel half-max times as new image. This image provides a visual indicator of the weld's quality because the shortest half-max times are expected at the weld nugget if the weld is properly constructed. If the half-max times in the welded area are longer than allowed for a particular alloy and sheet metal thickness, the weld is rejected because the longer half-max times indicate thermal transit delays caused by imperfections in the weld. Similarly, if the number of pixels with acceptably short times is less than the minimum area allowed by a predetermined standard for weld nugget size, the weld is rejected because the small number of acceptable pixels indicates that the weld nugget area is unacceptably small.

Figure 4A:
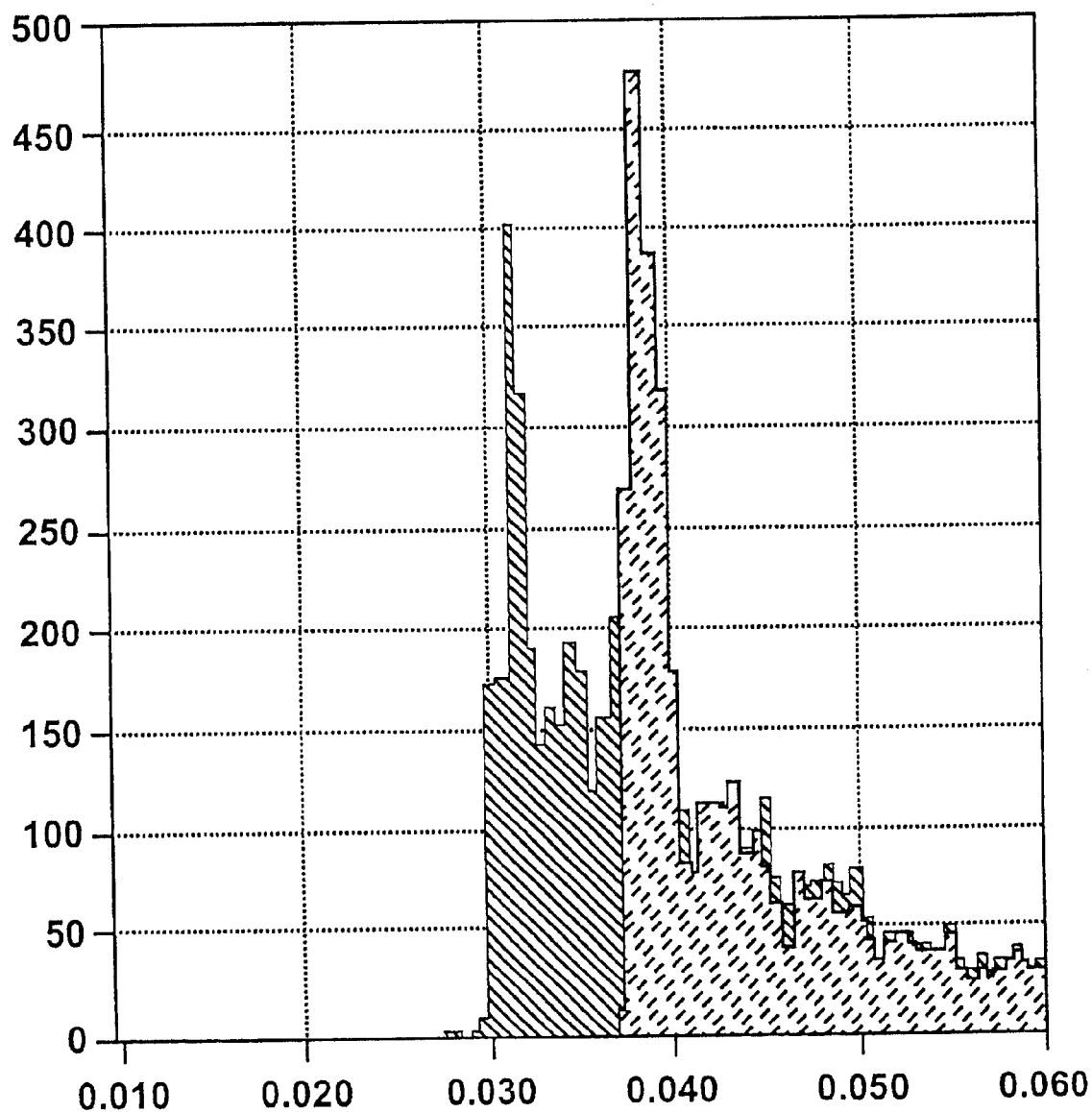
FIGS. 4A and 4B are examples of histograms that can be used to evaluate weld quality.
Figure 4B:
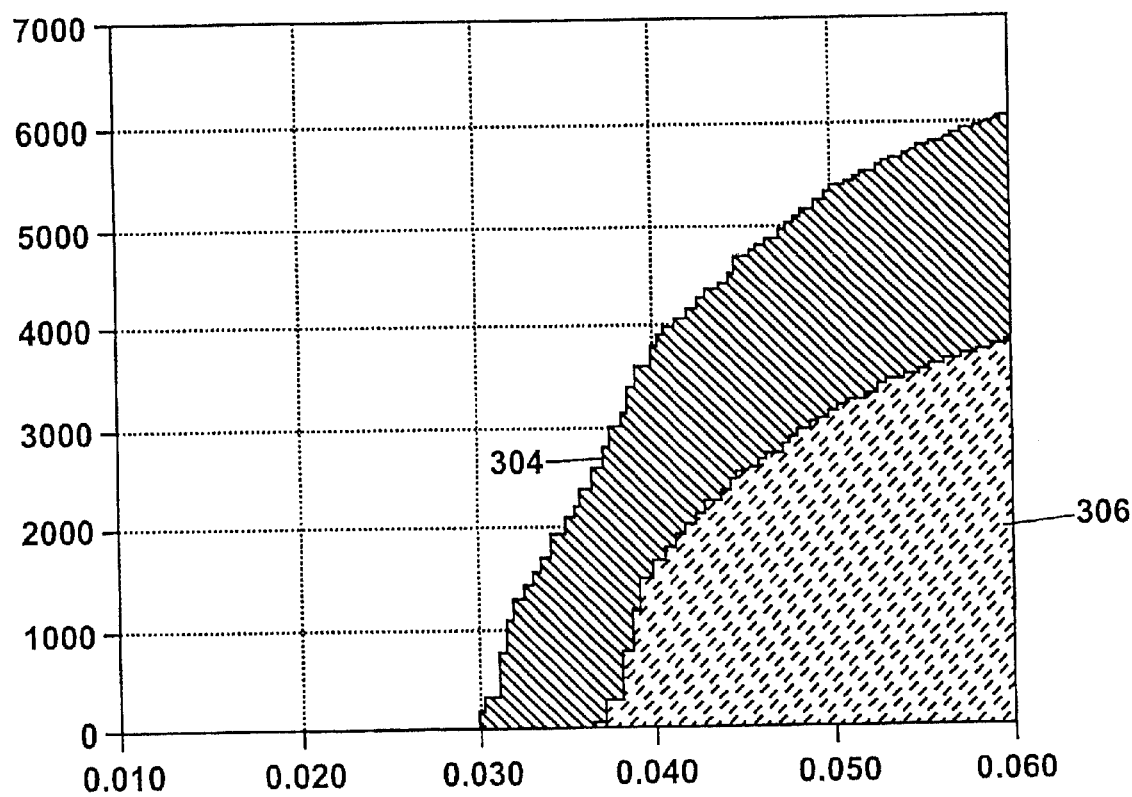

Referring to FIGS. 4A and 4B, the image of the half-max time described above is useful for visualizing the weld quality, but does not easily lend itself to an automated process. Evaluating the weld quality using an integral of the half-max time image as well as the original half-max time image, as illustrated in FIGS. 4B and 4A, respectively, provides the capability for automated weld evaluation. In FIG. 4A, the half-max time for each pixel in the image obtained from the IR camera is used to generate a two-dimensional array, or a histogram, that documents the half-max times appearing in the image and the number of pixels exhibiting each half-max time. The number of pixels that occur within a given time interval of this histogram represent the thermal flux through the weld region. The histogram of a good weld will indicate a flux value greater than some threshold value during the time interval that begins at the onset time, i.e. the time at which the first arrival of heat transmitted through the sample occurs. Further, the number of pixels can be directly correlated to area by performing a one time calibration process consisting of placing a ruler or other object of known length and width in the IR camera's field of view and dividing the linear dimension by the number of pixels spanned. Thus, the half-max time histogram can provide a great deal of information about the physical characteristics of the weld without requiring any user to observe the image generated by the IR camera.

Once the half-max time histogram has been created, weld acceptance and rejection decisions can be made on the basis of the total number of pixels having a half-max time that falls below a chosen threshold time. It is important to note that we are measuring the thermal flux, as it reaches the back surface, and not the mere absolute velocity of temperature change. This is an important consideration, because in actual automated welding operations, the applied pressure of the weld gun may compress the molten material so that thickness variations are introduced as high as 30% of the nominal thickness. Although thickness variations will affect the transit time of heat through the weld, it will not affect the flux of heat through the weld. In order to compare separate welds that may have such thickness variations, a compensation adjustment can be made to the onset time of all welds to match that of a selected calibration standard.

FIG. 4A shows the histograms for a good weld 300 and a bad weld 302. The peak in each histogram 300, 302 indicates the half-max time for the greatest number of pixels in the image. As can be seen in the Figure, the good weld histogram 300 has a peak around 30 milliseconds, while the bad weld histogram 302 has a peak around 40 milliseconds, indicating that a large number of pixels in the bad weld have unacceptably long half-max times.

For automation purposes, the flux as measured by the integral of the half-time histogram is particularly useful. FIG. 4B illustrates the calculation of the flux using the integral of the half-max time histogram shown in FIG. 4A, again for a good weld 304 and a bad weld 306. As can be seen in FIG. 4B, the integrated histogram for the good weld 304 indicates that at 35 milliseconds after the heat pulse, approximately 2000 pixels on the good weld have half-max times shorter than 35 milliseconds, while the integrated histogram for the bad weld 306 indicates that no pixels have half-max times of 35 milliseconds or less. From these histograms, it is possible to evaluate whether the weld is good without having to actually view the image obtained from the IR camera, making it possible to automate the weld evaluation process.

Figure 5:
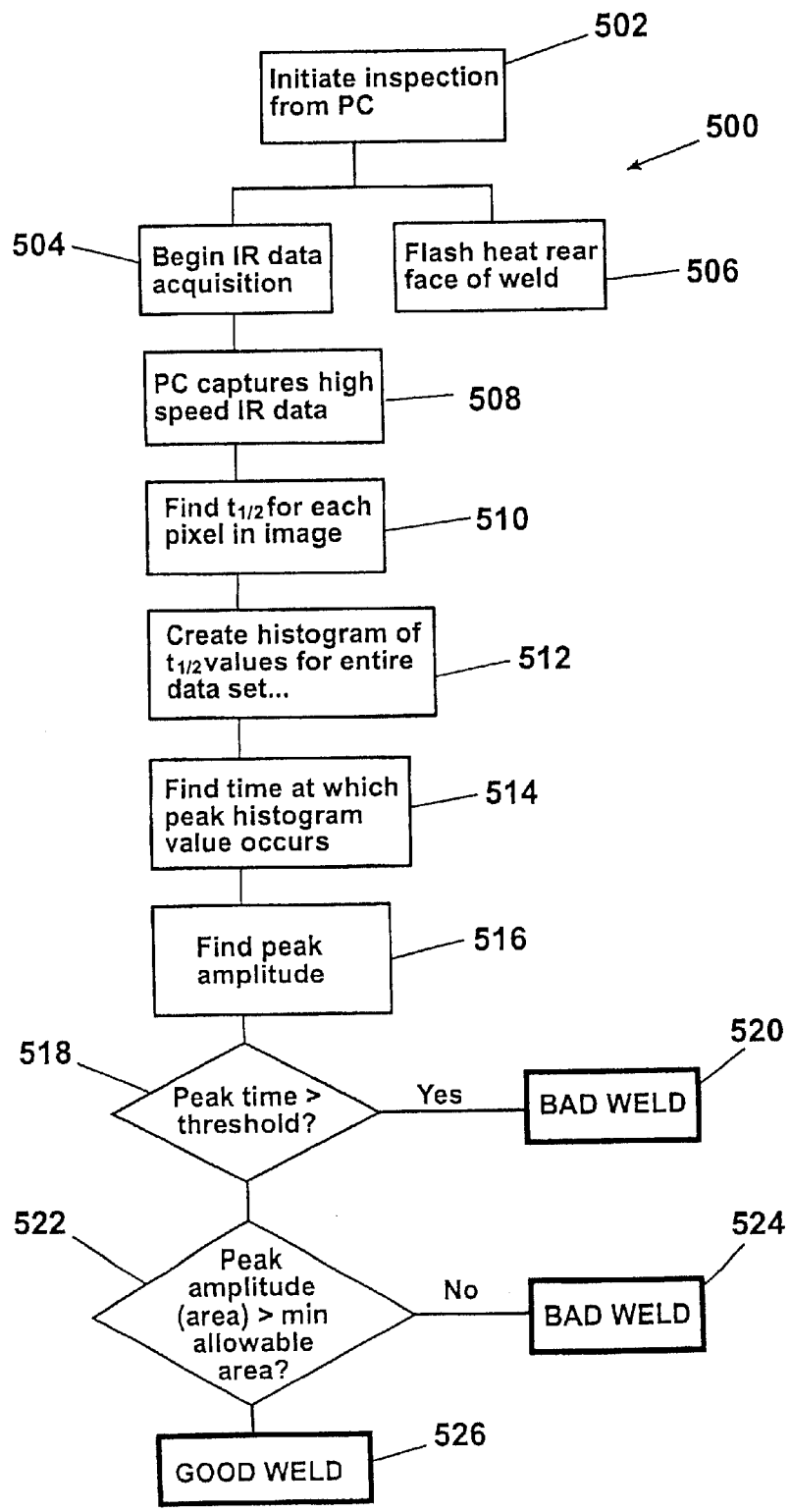
FIG. 5 is a flowchart illustrating a method according to the present invention.

FIG. 5 is a flowchart that describes one embodiment of the inventive method. As noted above, the method 500 begins with the computer initiating the weld inspection process at step 502. The welded sample is flash-heated at step 504, and image data capture begins at the same time as the flash heating step at step 506. Next, high-speed IR image data is captured and stored at step 508. The captured image data is used to calculate the half-max time or other time-temperature characteristic for each pixel in the image at step 510. The half-max time information is then used to generate at least one histogram, as explained above and as shown in FIGS. 4A and 4B, at step 512. The histogram is analyzed to find a peak time (i.e., the half-max time corresponding to the greatest number of pixels) and a peak histogram value, or a peak amplitude (i.e., the total number of pixels having a half-max time less than or equal to a particular half-max time, such as the peak time) at steps 514 and 516, respectively. This analysis can be conducted by integrating the half-max time histogram to obtain a second histogram, such as the one shown in FIG. 4B, but is not limited to such a method.

Once all of the peak time and peak amplitude information is obtained for the image, the method 500 determines whether the peak time exceeds a threshold value at step 518. Exceeding this threshold indicates a bad weld (step 520) because the heat flow is apparently slowed due to flaws in the weld. The method 500 also evaluates whether the peak amplitude (e.g., number of pixels) at the peak time, which corresponds to an area amount on the weld, is greater than a minimum allowable area at step 522. Falling below the minimum allowable area indicates a bad weld (step 524), even if the peak time falls below the threshold time in step 518, because it indicates that the weld nugget is not large enough to establish an acceptable bond. In other words, even if the largest number of pixels have a half-max time lower than a selected time threshold, the total number of pixels at the peak time may not be enough to create an acceptable weld. If the histogram generates acceptable results at steps 518 and 522, the weld is judged to be a good weld at step 526.

As can be seen from the above description, the method shown in FIG. 5 relies on objective criteria and does not require any human intervention or input. Thus, the process can be completely automated. Further, the objective criteria used in the invention provides an unambiguous way to set a weld quality threshold based on thermal transit time and the welded area size, removing the chance of inconsistent evaluations caused by subjective visual assessments. Because the weld quality can be characterized by the invention using two parameters, peak amplitude (weld nugget area) and peak time, the weld quality data can be archived and compared to other welds for process control. This capability does not exist for any known weld evaluation apparatus or method.

Figure 6:
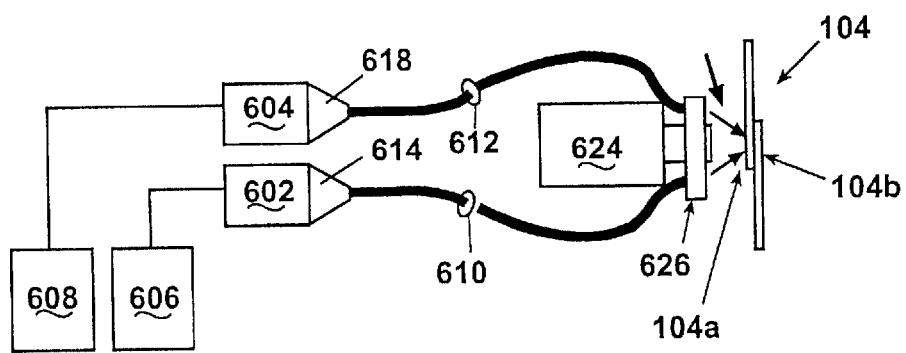
FIG. 6 is a third embodiment of the present invention using fiber optic bundles to transmit light energy from the flash lamp to the sample.

Now referring to FIG. 6, in a third embodiment, the present invention includes dual flashlamps 602, 604 which are electrically powered by their respectively associated power supplies 606, 608. Heat energy from flashlamp 602, 604 is delivered to sample 104 by way of a respectively associated optical fiber bundle 610, 612. Although the use of two flashlamps 602, 604 is the preferred embodiment, the current arrangement can be used with a single flashlamp or three or more flashlamps. In order to increase the transfer efficiency between the flashlamps and their respectively associated optical fiber bundles, a respectively associated concentrator 614, 618 is disposed between each flashlamp 602, 604 and its respectively associated optical fiber bundle 610, 612. The concentrator can be any number of well-known means for concentrating light such as a lens or a tapered snout reflector attached to each fiber bundle. In a preferred embodiment, each fiber bundle terminates adjacent a respectively associated lens 620, 622 (see FIG. 7B). Lenses 620, 622 reduce light beam divergence.

Figures 7A, 7B:
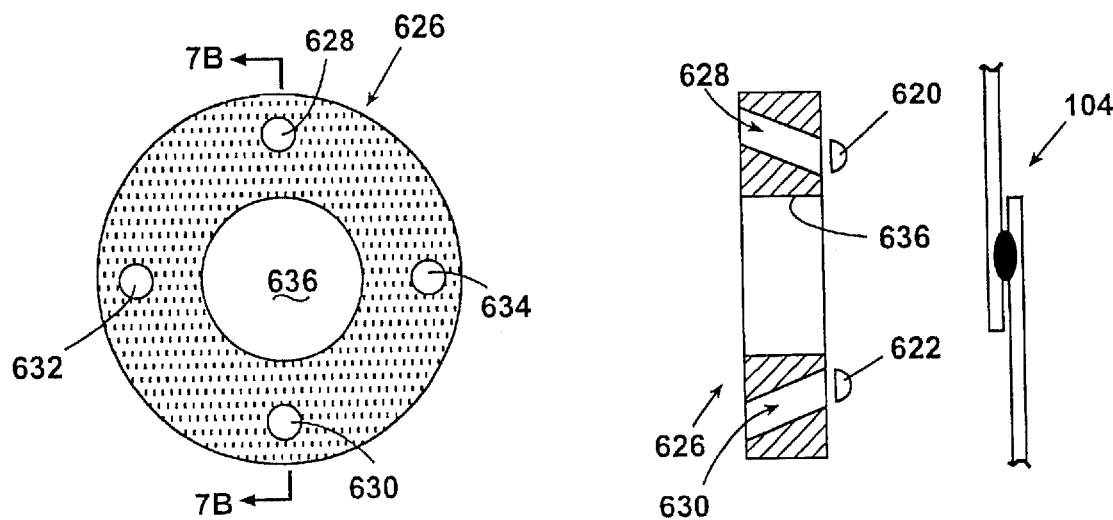
FIG. 7A is an enlarged view of the concentric collar, shown in FIG. 6, used to hold the IR camera and the fiber optic bundles.
FIG. 7B is a cross section taken substantially along lines 7B–7B of FIG. 7A.

Because optical fibers are inherently lossy, it may be necessary to use several flashlamps in order to deliver sufficient heat energy to the sample. Notwithstanding this inherent disadvantage in using optical fibers, there are a) fiber optic bundles are small (each bundle is on the order of 0.25 to 0.5 inches in diameter) and can be placed close to the sample surface, and b) because the heat source can be located far away from the exit end of the fiber bundle, the exit aperture of the fiber bundle does not experience any significant rise in temperature and accordingly does not introduce artifacts into the infrared image. Also, the flexibility of the fiber bundle is advantageous in some manufacturing situations, specifically where the imaging camera 624 and associated collar 626 may be mounted on a robot or actuator. One preferred configuration for this embodiment would be to house the exit ends of four fiber bundles in a respectively associated aperture 628 through 634 of collar 626 such that the exit ends of the bundles were aimed at the weld and at a prescribed distance from the weld. Collar 626 would be mounted concentrically to the lens of infrared camera 624 such that the camera lens and the convergence point of the light beams emanating from the fiber bundles coincide. FIGS. 7A and 7B disclose a preferred embodiment for collar 626. In this preferred embodiment aperture 636 is formed in the center of a generally cylindrical body. Four apertures 628, 630, 632, and 634 are spaced equally around aperture 636 and form the means for carrying a respectively associated optical fiber bundle. Preferably each aperture 628, 630, 632, and 634 is terminated by a lens (see for example lenses 620, and 622 covering apertures 628, and 630 respectively) for reducing light beam divergence. Collar 626 can be constructed from any material which is capable of withstanding the mechanical and heat loads associated with the environment in which the present invention is used. It is anticipated that materials such as aluminum, steel, plastic, reinforced resins, or the like will be preferred materials in the construction of collar 626.

The present invention is therefore a method and apparatus that tests weld quality without destroying the weld during testing. The invention can determine both the size of the weld and the quality of the bond via the weld's time-temperature characteristics allowing the invention to evaluate weld quality with no human intervention.

It should be understood that various alternatives to the embodiments of the invention described herein may be employed in practicing the invention. For example the present invention has been discussed in the context of examining weld integrity; however, it is contemplated that the present invention can be used in any application where the quality of the bond between two joined materials is at issue. Such applications could include examining adhesively joined laminated materials or materials whereby a base member is coated or painted by one or more deposited materials. It is intended that the following claims define the scope of the invention and that the method and apparatus within the scope of these claims and their equivalents be covered thereby.

What is claimed is:

1. An apparatus for non-destructive evaluation of a weld in a sample, comprising:
    a heater that heats a surface of the sample;
    a heat-detecting camera that collects temperature data from the sample over a selected time period; and
    a computer coupled to the heat-detecting camera to monitor a time-temperature characteristic from the temperature data and to compare the time-temperature characteristic with a predetermined standard indicating weld quality wherein the sample has a first surface and a second surface, and wherein the heater is disposed opposite the first surface and the heat-detecting camera is disposed opposite the second surface wherein the heater heats the first surface of the sample and the heat-detecting camera monitors the temperature of the second surface, and wherein the computer measures a time interval between the initiation of the heating and the time at which at least a portion of the second surface reaches a predetermined temperature level wherein an image generated by the heat-detecting camera is made of a plurality of pixels, and wherein the computer generates a histogram representing a thermal flux through the weld region.

2. The apparatus of claim 1, wherein the heater is selected from the group consisting of a flashlamp, pulsed laser, optical fiber, and light source coupled with a focusing lens.

3. The apparatus of claim 1, wherein the histogram reflects a half-max time for each pixel in the image, which indicat4es the time at which the temperature for the pixel reaches half its maximum temperature.

4. The apparatus of claim 3, wherein the computer evaluates the weld by comparing at least one of a peak time and a peak amplitude indicated in the histogram to at least one threshold value.

5. The apparatus of claim 1, further comprising a mirror that reflects visible light but passes infrared light, wherein the heat-detecting camera and mirror are disposed opposite a first surface of the sample and wherein the heater is disposed to reflect the visible light onto the first surface of the sample.

6. The apparatus of claim 5, wherein the heater heats the first surface of the sample and the heat-detecting camera monitors the temperature of the first surface, and wherein the computer measures a time interval between the initiation of the heating and the time at which at least a portion of the first surface cools to a predetermined temperature level.

7. The apparatus of claim 6, wherein an image generated by the heat-detecting camera is made of a plurality of pixels, and wherein the computer generates a histogram representing the thermal flux through the weld region.

8. The apparatus of claim 7, wherein the histogram reflects a half-max time for each pixel in the image, which indicates the time at which the temperature for the pixel reaches half its maximum temperature.

9. The apparatus of claim 8, wherein the computer evaluates the weld by comparing at least one of a peak time and a peak amplitude indicated in the histogram to at least one threshold value.

10. The apparatus of claim 1, wherein an image generated by the heat-detecting camera is made of a plurality of pixels, and wherein the computer generates a histogram representing the time-temperature characteristic for each pixel in the image and evaluates the weld by comparing the time-temperature characteristic with an objective threshold.

11. The apparatus of claim 10, wherein the computer evaluates at least one of a maximum amplitude, ascending slope, descending slope, and maximum time of the time-temperature characteristic to evaluate the weld.

12. The apparatus of claim 1, further including a conical snout disposed between said heater and said sample for concentrating the heat generated by the heater upon the surface of the sample.

13. A method of for non-destructive evaluation of a weld in a sample, comprising the steps of:
    heating the sample;
    capturing a plurality of infrared images of the sample over time;
    determining a time-temperature history of the sample; and
    comparing a time-temperature characteristic in the time-temperature history with a threshold value to evaluate the weld wherein the determining step further includes the steps of:
        obtaining a time-temperature characteristic for each pixel in the plurality of images;
        creating a least one histogram based on all of the time-temperature characteristics from the obtaining step.

14. The method of claim 13, wherein the heating and capturing steps include the steps of:
    heating a first surface of the sample; and
    capturing a plurality of infrared images of a second surface of the sample over time.

15. The method of claim 14, wherein the comparing step includes comparing at least one time-temperature characteristic selected from the group consisting of thermal flux through the weld region, a maximum amplitude, an ascending slope, a descending slope, maximum time value of the time-temperature history with the threshold.

16. The method of claim 13, wherein the heating and capturing steps include the steps of:
    heating a first surface of the sample; and
    capturing a plurality of infrared images of the first surface of the sample over time.

17. The method of claim 10, wherein the comparing step includes comparing at least one time-temperature selected from the group consisting of a maximum amplitude, an ascending slope, a descending slope, and maximum time of the time-temperature history.

18. The method of claim 13, wherein the time-temperature characteristic is a half-max time.

19. The method of claim 13, wherein the time-temperature characteristic is a half-max time, wherein the crating step includes the step of generating a first histogram indicating a peak time, which corresponds to the half-max time associated with the greatest number of pixels; and generating a second histogram indicating a peak amplitude, which corresponds to a total number of pixels having a half-max time less than or equal to a selected half-max time.

20. The method of claim 19, wherein the selected half-max time for determining the peak amplitude is the peak time.

21. An apparatus for non-destructive evaluation of a weld in a sample, comprising:

a heater that heats a surface of the sample;

a heat-detecting camera that collects temperature data form the sample over a selected time period; and a computer coupled to the heat-detecting camera for monitoring a time-temperature characteristic from the temperature data, and for comparing the time-temperature characteristic with a predetermined standard indicating weld quality, wherein said computer further includes means for using said temperature data for generating a histogram representing a thermal flux through a weld region.

22. The apparatus of claim 21, wherein the heater is selected from the group consisting of a flashlamp, pulsed laser, optical fiber, and light source coupled with a focusing lens.

23. The apparatus of claim 21, wherein the sample has a first surface and a second surface, and wherein the heater is disposed opposite the first surface and the heat-detecting camera is disposed opposite the second surface.

24. The apparatus of claim 23, wherein the heater heats the first surface of the sample and the heat-detecting camera monitors the temperature of the second surface, and wherein the computer measures a time interval between the initiation of the heating and the time at which at least a portion of the second surface reaches a predetermined temperature level.

25. The apparatus of claim 21, wherein an image generated by the heat detecting camera is made from a plurality of pixels, and wherein the histogram reflects a half-max time for each pixel in the image, which indicates the time at which the temperature for the pixel reaches half its maximum temperature.

26. The apparatus of claim 25, wherein the computer evaluates the weld by comparing at least one of a peak time and a peak amplitude indicated in the histogram to at least one threshold value.

27. An apparatus for non-destructive evaluation of a weld in a sample, comprising:

a heater for heating a surface of the sample;

a heat-detecting camera for collecting temperature data from the sample over a selected time period; and a computer coupled to the heat-detecting camera for using the temperature data for determining a half-max time and for comparing the half-max time with a predetermined standard indicating weld quality.

28. The apparatus of claim 27, wherein the heater is selected from the group consisting of a flashlamp, pulsed laser, optical fiber, and light source coupled with a focusing lens.

29. The apparatus of claim 27, wherein the sample has a first surface and a second surface, and wherein the heater is disposed opposite the first surface and the heat-detecting camera is disposed opposite the second surface.

30. The apparatus of claim 29, wherein the heater heats the first surface of the sample and the heat-detecting camera monitors the temperature of the second surface, and wherein the computer measures a time interval between the initiation of the heating and the time at which at least a portion of the second surface reaches a predetermined temperature level.

31. The apparatus of claim 30, wherein an image generated by the heat-detecting camera is made of a plurality of pixels, and wherein the computer generates a histogram representing a thermal flux through the weld region.

32. The apparatus of claim 31, wherein the histogram reflects the half-max time for each pixel in the image, which indicates the time at which the temperature for the pixel reaches half its maximum temperature.

33. The apparatus of claim 32, wherein the computer evaluates the weld by comparing at least one of a peak time and a peak amplitude indicated in the histogram to at least one threshold value.

34. A method for non-destructive evaluation of a weld in a sample, comprising the steps of:

heating the sample;

capturing a plurality of infrared images of the sample over time;

determining a half-max time-temperature history of the sample; and comparing the half-max time-temperature history of the sample with a threshold value to evaluate the weld integrity.

35. The method of claim 34, wherein the heating and capturing steps include the steps of:

heating a first surface of the sample; and capturing a plurality of infrared images of a second surface of the sample over time.

36. The method of claim 34, wherein the heating and capturing steps include the steps of:

heating a first surface of the sample; and capturing a plurality of infrared images of the first surface of the sample over time.

37. The method of claim 34, wherein the determining step includes the steps of:

obtaining a time-temperature characteristic for each pixel in the plurality of images;

creating at least one histogram based on all of the time-temperature characteristics from the obtaining step.

38. The method of claim 37, wherein the creating step includes the step of generating a first histogram indicating a peak time, which corresponds to the half-max time associated with the greatest number of pixels; and generating a second histogram indicating a peak amplitude, which corresponds to a total number of pixels having a half-max time less than or equal to a selected half-max time.

* * * * *

UNITED STATES PATENT AND TRADEMARK OFFICE
CERTIFICATE OF CORRECTION

PATENT NO.    : 6,585,146 B2
DATED         : July 1, 2003
INVENTOR(S)   : Steven M. Shepard It is certified that error appears in the above-identified patent and that said Letters Patent is hereby corrected as shown below:

Column 7,
Line 48, delete "indicat4es" and replace with -- indicates --

Column 8,
Line 65, delete "crating" and replace with -- creating --

Column 9,
Line 12, delete "form" and replace with -- from --

Signed and Sealed this

Twenty-first Day of October, 2003

JAMES E. ROGAN
*Director of the United States Patent and Trademark Office*